(12) United States Patent
Hochman

(10) Patent No.: US 6,652,482 B2
(45) Date of Patent: Nov. 25, 2003

(54) DENTAL ANESTHETIC AND DELIVERY INJECTION UNIT WITH AUTOMATED RATE CONTROL

(75) Inventor: Mark N. Hochman, Lake Success, NY (US)

(73) Assignee: Milestone Scientific Inc, Livingston, NJ (US)

( * ) Notice: Subject to any disclaimer, the term of this patent is extended or adjusted under 35 U.S.C. 154(b) by 0 days.

(21) Appl. No.: 09/931,398

(22) Filed: Aug. 16, 2001

(65) Prior Publication Data

US 2002/0052575 A1 May 2, 2002

Related U.S. Application Data

(60) Provisional application No. 60/226,446, filed on Aug. 18, 2000.

(51) Int. Cl.$^7$ .......................... A61M 31/00; A61M 1/00; A61M 37/00
(52) U.S. Cl. .......................... 604/65; 604/131; 604/118
(58) Field of Search ........................ 604/131, 153, 604/22, 65, 151, 118; 606/159, 41, 1, 106, 108; 600/407, 182, 478, 104; 417/53, 313; 607/101

(56) References Cited

U.S. PATENT DOCUMENTS

| 4,464,172 A | * | 8/1984 | Lichtenstein ......... 128/DIG. 13 |
| 4,559,038 A | | 12/1985 | Berg et al. |
| 4,747,824 A | | 5/1988 | Spinello |
| 4,755,172 A | | 7/1988 | Baldwin |
| 5,180,371 A | | 1/1993 | Spinello |
| 5,423,740 A | | 6/1995 | Sullivan et al. |
| 5,690,618 A | | 11/1997 | Smith et al. |
| 5,868,728 A | * | 2/1999 | Giungo et al. .................. 606/1 |
| 5,906,597 A | | 5/1999 | McPhee |
| 6,022,337 A | * | 2/2000 | Herbst et al. ................ 604/131 |
| 6,080,170 A | * | 6/2000 | Nash et al. .................. 606/159 |
| 6,140,452 A | | 10/2000 | Felt et al. |
| 6,179,804 B1 | | 1/2001 | Satterfield |
| 6,321,106 B1 | * | 11/2001 | Lemelson .................... 600/182 |

OTHER PUBLICATIONS

PCT International Search Report dated Apr. 9, 2002; PCT/US01/41746; claiming priority to US patent application Ser. No. 09/931,398.

* cited by examiner

Primary Examiner—Michael J. Hayes
Assistant Examiner—Roz Ghafoorian
(74) Attorney, Agent, or Firm—Gottlieb, Rackman & Reisman, P.C.

(57) ABSTRACT

An improved injection device is operated in a manual mode in which it delivers a liquid drug to a patient at a rate determined all the time by a control member, and a cruise control mode in which the preselected rate is maintained by the controller after the control member is released by a clinician. The control member may be used to select one of two liquid delivery rates, or alternatively a delivery rate may be selected which may have values between an upper and a lower limits. If the device is operated in the cruise control mode, an override switch must be activated to reset the rate.

15 Claims, 4 Drawing Sheets

DENTAL ANESTHETIC AND DELIVERY INJECTION UNIT WITH AUTOMATED RATE CONTROL

RELATED APPLICATIONS

This application claims the benefit of U.S. Provisional Patent Application Ser. No. 60/226,446 filed Aug. 18, 2000.

BACKGROUND OF THE INVENTION a. Field of Invention

This invention pertains to an automated anesthetic delivery apparatus particularly suited for the dental and medical fields, and more particularly to an apparatus and method in which the rate is controlled and maintained automatically until reset or otherwise changed by the operator.

b. Description of the Prior Art

While local anesthetics eliminate the often excruciating pain that would otherwise be suffered during medical procedures, dental extractions, drilling, etc., the medical and dental patient is still subject to pain from the hypodermic injection of the anesthetic into the local tissues of the body.

It is well established that more than 50% of adult patients fear injections in general, and even a greater number especially fear injections in the mouth during a dental procedure.

Accordingly, it would be desirable to provide a medical and dental anesthetic injection delivery system which substantially eliminates the pain suffered by a patient during injection of anesthetic into the mouth or other tissues of the body.

U.S. Pat. No. 6,022,337, incorporated herein by reference generally describes a local anesthetic delivery system which renders the nerve bundles which supply the teeth and supporting dental structures disabled in the area of the injection and in the path of the needle before a pain sensation is perceived by the patient. The system comprises a drive unit for selectively delivering anesthetic through a controllable handpiece unit which carries a needle for tissue penetration. Operation of the drive unit can be selectively controlled so that different amounts of anesthesia may be delivered through the needle, depending upon whether the practitioner is either penetrating the tissue or has otherwise reached the location within the tissue where nerve disability is required.

The system uses a linear activator to deliver a controlled amount of anesthetic from a cartridge that is locked into the drive unit. The drive unit which can be operated by a foot pedal that is selectively depressed in order to deliver anesthetic through the handpiece unit.

The system is designed to accommodate a local anesthetic cartridge and a variety of needle sizes. The drive unit of the system includes a motor and an on-board microprocessor to facilitate control of anesthetic flow. The drive unit, utilizing the technology described in U.S. Pat. Nos. 4,747,824 and 5,180,371, and incorporated herein by reference, enables delivery of an anesthetic solution at a constant pressure and volume, regardless of variations in tissue resistance. At the delivery end of the needle, the system delivers a minute amount of the anesthetic which precedes the needle during injection in the dental tissue, creating in effect an anesthetic pathway. The combination of an anesthetic pathway and controlled pressure and volume (flow rate) results in an effective and pain-free injection. Importantly, the system further incorporates foot pedal 29 is operatively connected to air hose 31, which in turn is coupled to a pressure sensor 64 located inside unit 13. In operation of system 11, the pressure change from pedal 29 is detected by the sensor 64. Sensor 64 then generates a corresponding control signal used to control the flow of the anesthetic solution. In the preferred embodiment, as described in more detail below, when foot pedal 29 is slightly or partially depressed, system 11 operates at a slow speed. When foot pedal 29 is firmly or fully depressed, system 11 operates at a faster speed. The system can be programmed to have multiple rates of flow, not limited to two speeds.

While this system operates satisfactorily, some physicians or dentists may not be completely satisfied with it because it requires the pedal to be maintained in a certain position for an extended time period.

OBJECTIVES AND SUMMARY OF THE INVENTION

Accordingly, it is an object of the invention to provide a local anesthetic delivery injection system which can be used for all known medical and dental injection procedures and having an improved automatic mode of operation.

A further objective is to provide a device which reduces the strain on the dentist or other health care practitioner for extended injection sections.

A further objective is to provide an injection device that has an automated mode of operation that allows the physician, dentist or health practitioner to devote his attention to other details and pay attention to the system only when a change in its operation is required.

Yet another object of the invention is to provide a dental anesthetic injection delivery system which enhances the precision and accuracy of anesthetic delivery.

Still other objects and advantages of the invention will in part be obvious, and will in part be apparent from the following description. Briefly, an injection device constructed in accordance with this invention includes an electrically controlled pump, a handle terminating in a needle through which the medication is ejected and a foot switch or other similar control means (i.e., hand control) used to activate the pump controller. The control means may have several positions. In one embodiment, the control means includes three positions: OFF, SPEED 1 and SPEED 2. The pump is off in the off position, at SPEED 1 the medication is administered at a first flow rate, and at SPEED 2 the pain killer is administered at a second, higher flow rate. Alternatively the control means may be adapted to have either many discrete positions or could be adjusted continuously between the SPEED 1 and SPEED 2 positions and the flow rate may be changed substantially continuously between an upper and a lower speed limit. Preferably the control means may be spring loaded or otherwise biased, so that when it is SPEED 1 or SPEED 2 position and is then released, it goes to the OFF position automatically. Importantly, according to this invention, the pump controller is provided with several modes of operation. In one mode of operation, which may be termed a manual mode, the pump controller monitors the position of the control means continuously and operates the pump in a responsive manner so that if the control means is in the SPEED 1 position, the pump is operated at SPEED 1, in the SPEED 2 position, the pump is operated at SPEED 2 (and fluid is delivered at a corresponding rate) and if the control means is in the OFF position, the pump motor is turned off, or it goes into an automatic aspiration mode. Another mode of operation is a so-called cruise control mode. In this mode of operation the pump controller operates in a manner similar to a cruise control in a car. More particularly, in the cruise control mode, when control means is released, the pump controller maintains the previous operation of the pump until a separate control means such as an override switch is activated to change the mode of operation of the pump. This separate control means may consist of a separate push button on the handle, on the controller or on the pedal switch. It may also be achieved as currently embodied via software configuration. A "window" of time exists in which removal of ones foot from the foot control activates "cruise-control". This "window" may be defined within the software and activated by removal of the foot control.

The invention is also applicable to other medical and/or dental devices such as ultrasonic scalers, polishing devices, and other rotary and electronic instruments which are operated by a clinician at a controlled rate or speed.

In one aspect, the invention pertains to an injection device adapted to inject a therapeutic liquid into a patient under the control of a clinician, said device comprising a handle adapted to be held by a clinician for administering the liquid; a pump adapted to selectively deliver the liquid to said handle; a motor adapted to operate said pump at a selected rate in accordance with a control signal; control member operated by the clinician to select said rate, said control member having a first position associated with the selected rate and a second position; and a microprocessor coupled to said control member and adapted to generate said control signal after said control member has been operated and released by the clinician to generate said control signal.

BRIEF DESCRIPTION OF THE DRAWINGS

For a fuller understanding of the invention, reference is made to the following description, taken in connection with the accompanying drawings, in which.

DETAILED DESCRIPTION OF THE INVENTION

Figure 1:
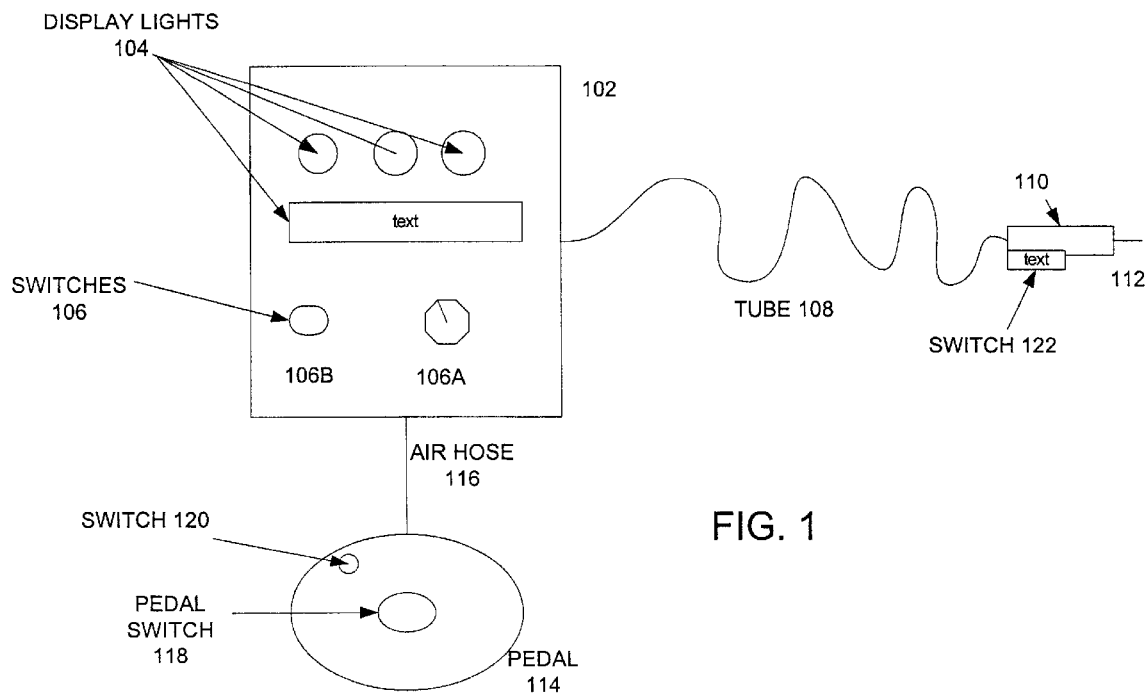
FIG. 1 shows a somewhat schematic representation of an injection device constructed in accordance with this invention.
Figure 2:
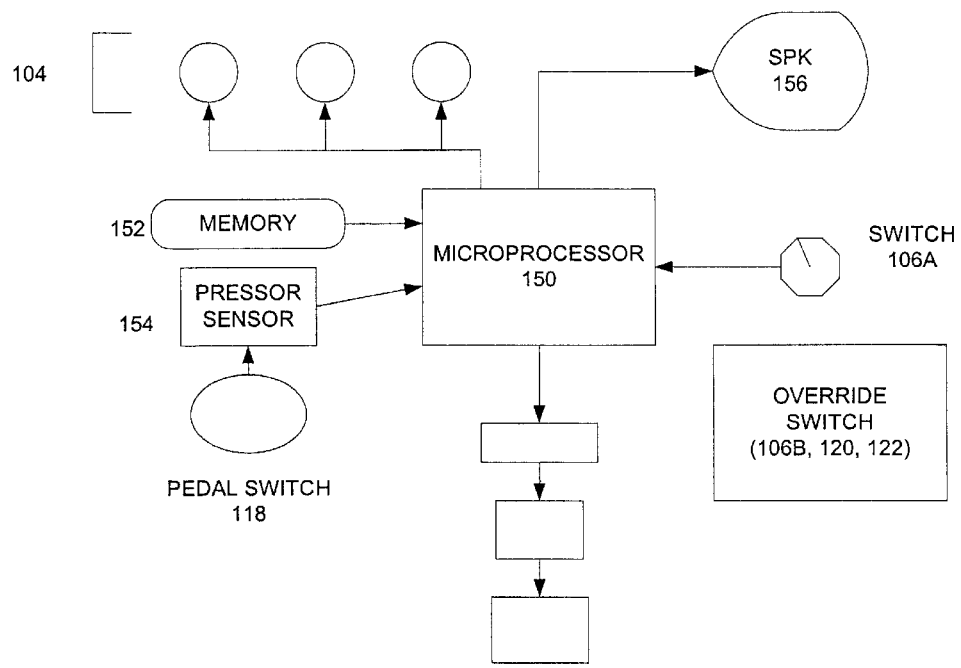
FIG. 2 shows a block diagram of the device of FIG. 1; shows a manual mode of operation of the injection device of FIG. 1.

FIGS. 1 and 2 show generically a device 100 can be used to inject or otherwise introduce (and, selectively aspirate) a liquid into a patient. As shown in the Figures, device 100 includes a housing 102 with a plurality of indicators 104, and control buttons 106 or other user selectable data and command input means. One of the control buttons 106 is a rotatable knob 108 having a plurality of positions, as discussed in more detail below.

Disposed in or otherwise associated with the housing is a reservoir containing a drug, an anesthetic or other liquid that may be used by a doctor or other health care provider to perform a medical or dental procedure on the patient.

Device 100 further includes an elongated tube 108 having one end attached to the housing 102 and the other end attached to a handle 110. The handle 110 includes a syringe 112.

Device 100 further includes a foot pedal 114 attached to the housing 116 by an air hose 116. The pedal 114 is made with a primary foot control element 118 having three or more positions, as discussed in more detail below. Also mounted on the pedal 114 is a second control element 120.

FIG. 2 shows a block diagram of the electrical elements of the device 100. The device includes a microprocessor 150 which operates in accordance with programming stored in a memory 152 and control signals received from control switches 106. As seen in the Figure, the air hose 116 is connected to a pressure sensor 154 which generates an electrical signal indicative of the position of the foot pedal switch 118. The microprocessor provides visual indication and prompts to the operator through indicators 104 and oral indications and prompts through a speaker 156.

The primary purpose of the microprocessor 150 is to control the operation of a motor 158. The motor receives control commands from the microprocessor 150 and in response activates a pump 160. The pump 160 is coupled to a source or reservoir of liquid 162 and is capable of either dispensing the liquid from the reservoir to tube 108, or, when reversed, it can withdraw liquid from the tube 108 into the reservoir 162. The pump 160 and reservoir 162 can be implemented in many forms. For example, the pump 160 and reservoir 162 can be implemented as a syringe with a piston reciprocated by a rod coupled to motor 158.

The elements shown in FIG. 2 can be disposed in housing 102. Alternatively, at least some of the elements, including the motor 158, reservoir 162 and pump 160 may be disposed in handle 110, in which case the tube 108 may be replaced by an electrical connector.

Figure 3:
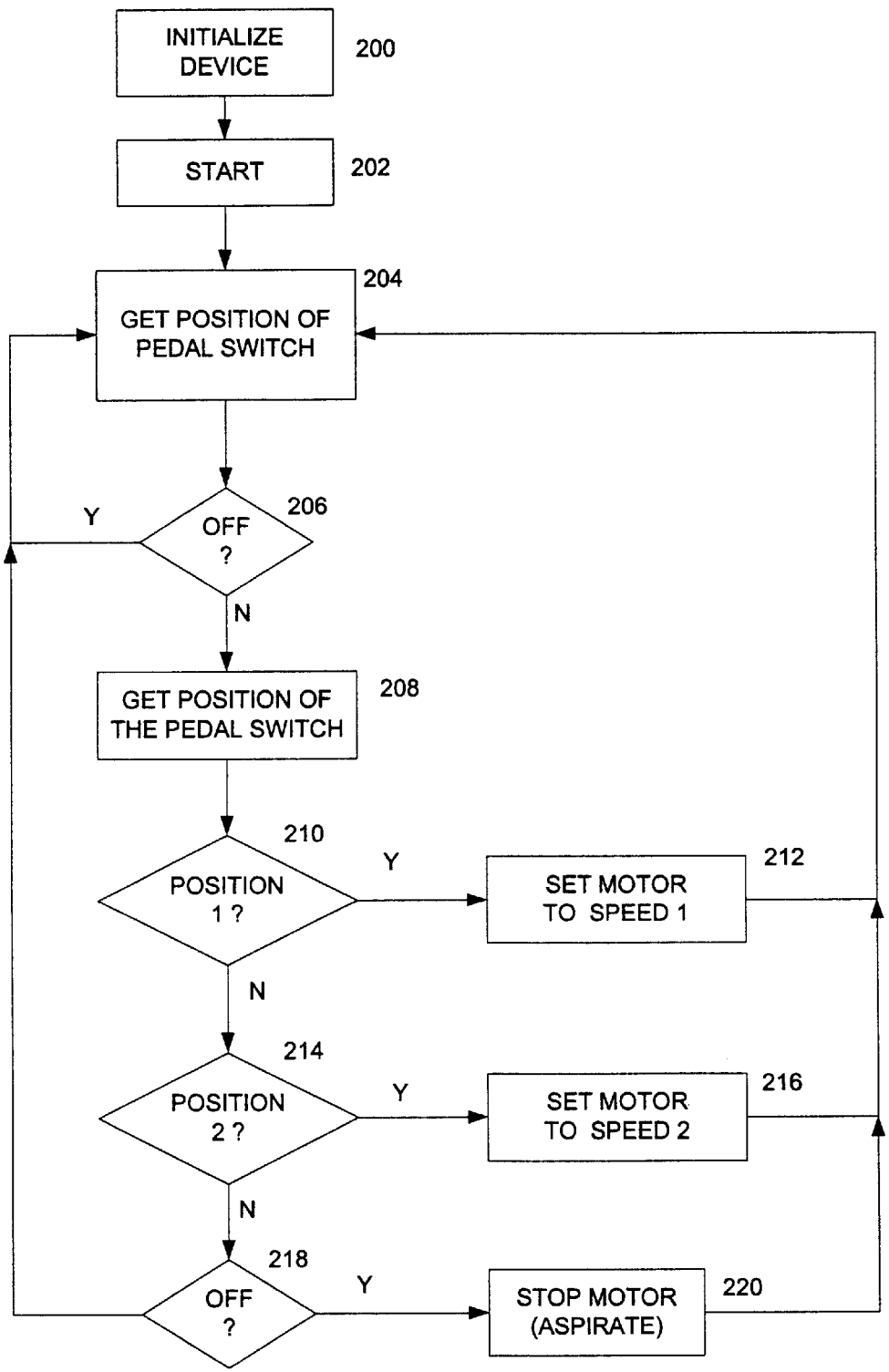
FIG. 3 shows a flow chart showing the operation of the device of FIGS. 1 and 2 in a manual mode.
Figure 4:
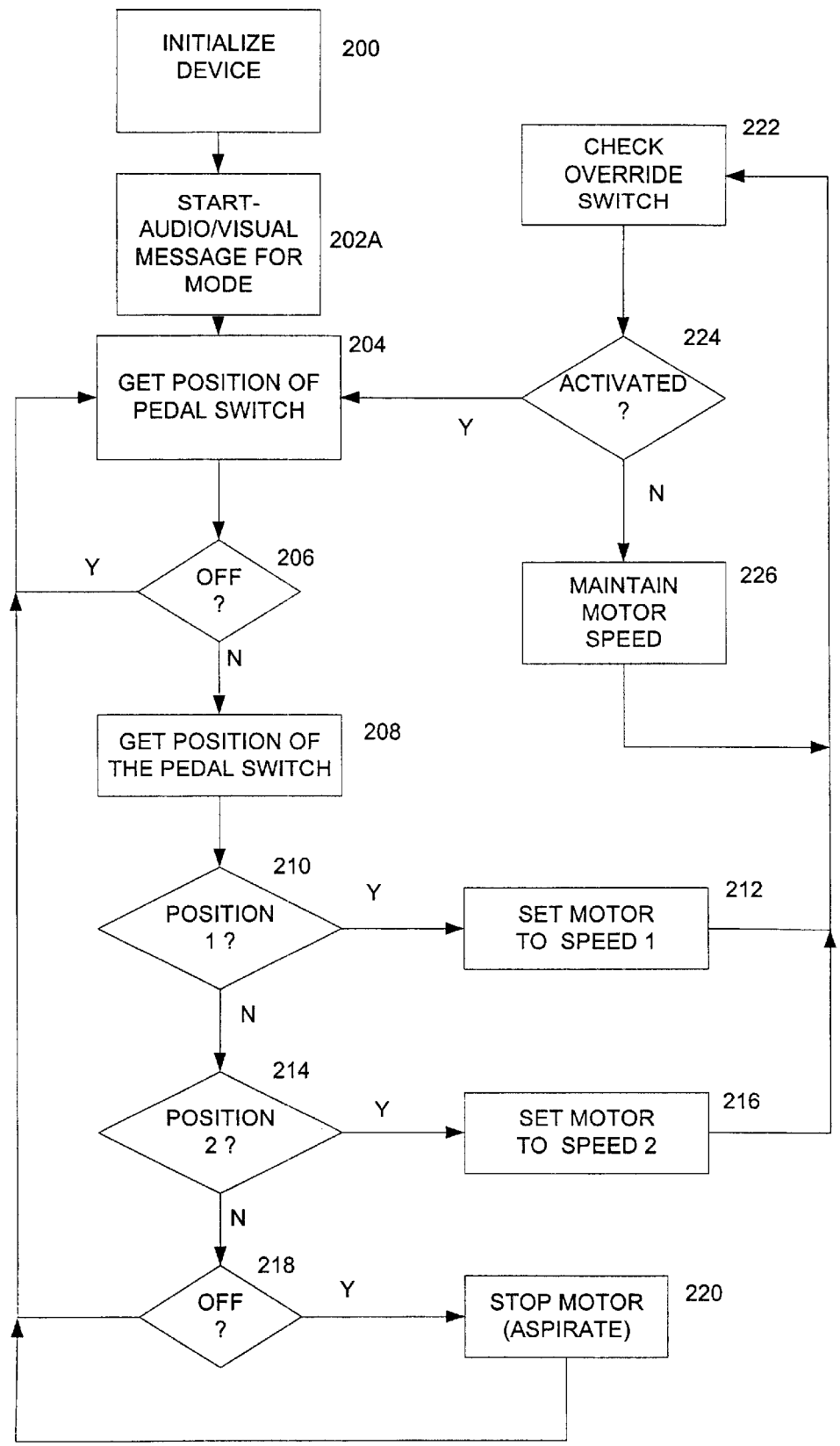
FIG. 4 shows a cruise control mode of operation of the injection device of FIGS. 1 and 2.

Device 100 can be operated in several modes. The mode of operation is determined by the position of the knob 106B. For one position of the knob, the device 100 operates in the same manner as the prior injection devices. In this mode the operation of the device 100 can be characterized as a manual or semiautomatic mode in which the device is operated in response to control signals from the clinician. This mode of operation is now described in conjunction with the flow chart of FIG. 3. In step 200 the device is initialized. This step includes entering various operational parameters into memory 152, loading the reservoir 162 with the appropriate liquid, purging the tube 108, and needle 112, etc. When the clinician is ready for the injection, he pushed a button, such as 106B indicating that the start of the operation (step 202). Once the operation is started, the microprocessor 150 checks the position of the foot pedal switch 118 (step 204). If this switch is activated, as determined in step 206, then in step 208, the microprocessor 150 obtains the current position of the pedal switch 118. For example, the switch could have an off position, a position 1 and a position 2.

At step 210 a check is performed to determine if the switch is in position 1. If it is then in step 212 the microprocessor 150 sets the motor 158 to operate at a first speed. The microprocessor 150 then returns to step 208 and gets the new position of the pedal switch 118.

If in step 210 it is determined that the switch 118 is not in position 1 then in step 216 a check is performed to determine if the switch 118 is in position 2. If it is, then in step 216, the microprocessor sets the motor 158 to operate at a second speed 2. In an alternate embodiment, the speed of the motor 158 can be set in these steps to be anywhere between a lower and an upper limit. For this embodiment, the switch 118 must be capable of having a variable position between positions 1 and 2.

If the switch is not in position 2 then in step 218 the microprocessor checks if the switch 118 is in the off position. If it is then in step 220 the motor 158 is stopped. In an alternate embodiment, under certain conditions, the motor 158 in step 220 may be reversed for a short time period to induce aspiration. In addition, a separate switch (not shown) may be provided which would cause the motor to reverse. In any event, in the mode shown in FIG. 3, the microprocessor 150 checks the position of the switch 118 and adjusts the operation of the motor 158 accordingly.

As discussed above, in some instances this mode of operation may be unsatisfactory. Therefore according to this invention, the device 158 could be operated in a cruise control mode. This mode can be selected by changing the position of know 106A. In this mode, the device 100 operates as shown in a manner similar to the one shown in FIG. 3, with some exceptions. More particularly, in step 202A when the device operation is started, the clinician is advised of the selected mode of operation (i.e., in this case, cruise control). This step is accomplished by generating an audio message through speaker 156, a visual message on one of the displays, a combination audio/visual message or by other similar means.

In addition, after the requested motor is set in either of these steps, the microprocessor checks if an override switch is activated (step 222). This override switch can be set on the housing (see switch 106B, on the foot pedal-switch 120, on the handle-switch 124, and so on. If in step 224 it is determined that the override switch has not been activated, then in step 226 the previous speed of the motor 158 is maintained.

The microprocessor 150 continues to check the position of the override switch at regular intervals and during this time the motor is maintained at the previously selected speed. Since during steps 222, 224, 226 the position of the pedal switch 118 is not checked, after step 212 the clinician can release the pedal switch and allow it to return to a neutral or off position.

After the override switch is activated (the override switch is preferably a momentary switch) the clinician can use the pedal switch 118 to generate a new control signal for the motor (i.e., speed 1, speed 2, off, etc.)

Figure 5:
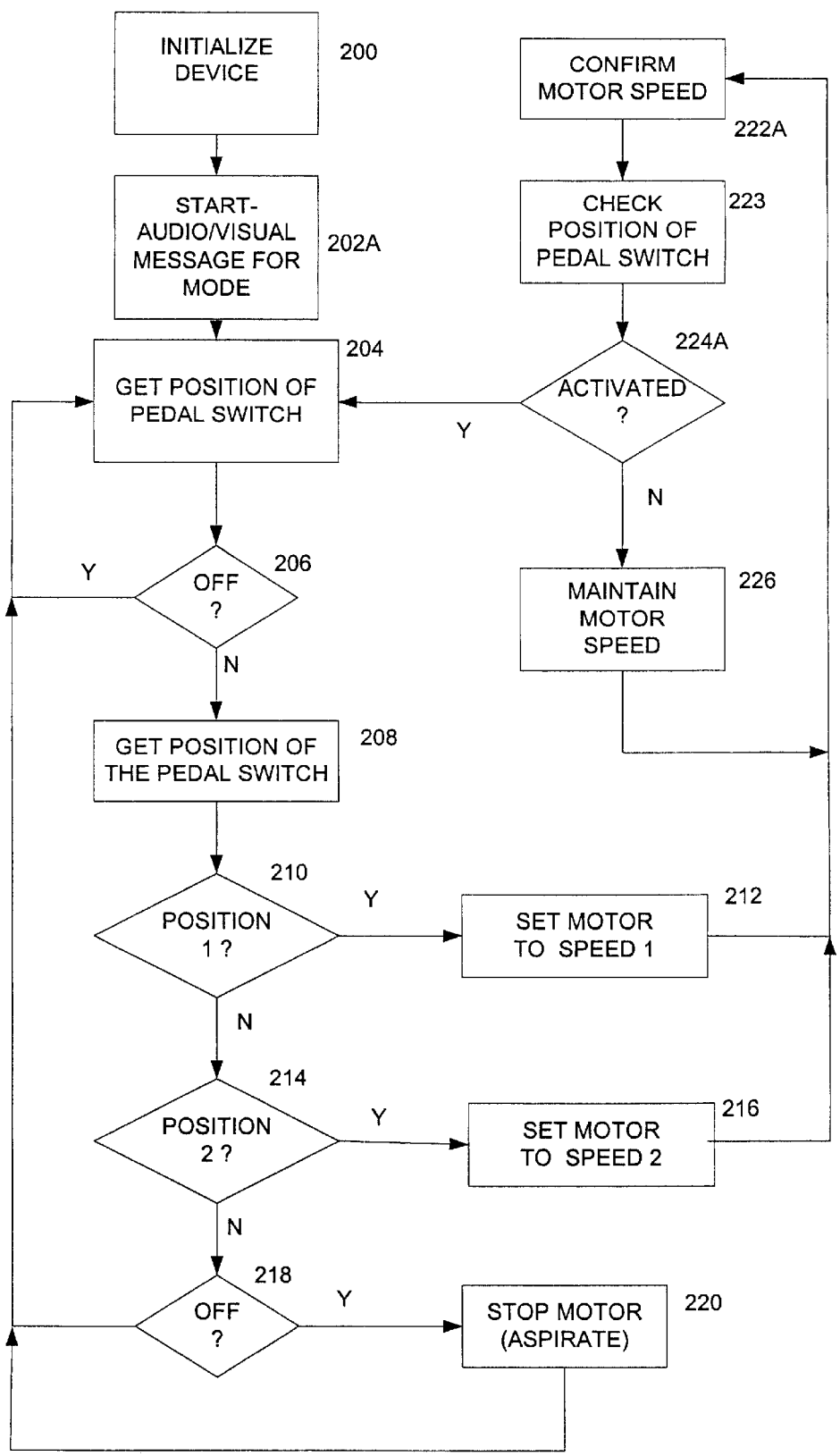
FIG. 5 shows an alternate mode of operation of the injection device of FIGS. 1 and 2.

Alternatively, as shown in FIG. 5, the function of the override switch can be implemented by software. In this embodiment, after the speed of the motor is set (in steps 212, or 216), this speed is confirmed in step 222A. That is, an indication (either visual, oral, or both) is given to the clinician to indicate what is the current speed of the motor. This indication is a trigger or prompt to the clinician to release the pedal switch and allow it to return to the neutral or off position. Then in step 223 the position of the pedal switch is checked. In step 224 a determination made as to whether the pedal switch has been activated or moved from its off position. If the pedal switch is still in the off position, the motor speed is maintained in step 226. If the pedal switch is reactivated, the microcomputer 150 returns to step 204.

In the embodiments disclosed above a specific type of injection device is described that is operated by a clinician through a multi-position foot pedal switch. Of course, other types of control means or members may be used as well to obtain a similar functionality. For example, switches or other control elements for controlling the dispensing of the liquid may be provided on the housing or on the handle.

It will thus be seen that the objects set forth above, among those made apparent from the preceding description, are efficiently attained, and since changes may be made without departing from the spirit and scope of the invention, it is understood that the above description is merely illustrative and does not otherwise limit the scope of the invention. The claims that follow define the inventive scope.

What is claimed is:

1. An injection device comprising:
   a delivery member adapted to deliver a therapeutic liquid at one of a first rate and a second rate;
   a microprocessor adapted to generate control signals to said delivery member; and
   a control member operable by an operator to select one of said first rate and second rates, wherein said microprocessor cooperates with said control member to maintain said delivery member at said selected rate after said control member is released by the operator;
   wherein said control member has a plurality of positions including a selection position defining a selected rate for said delivery member and a neutral position, wherein said control member is biased to said neutral position when released by the operator.

2. The device of claim 1 further comprising an override member operable by the operator, wherein said microprocessor is adapted to terminate the operation of said delivery member when said override member is operated.

3. The device of claim 1 wherein said delivery member is adapted to deliver said liquid at a rate that is adjustable between a lower and an upper limit.

4. The device of claim 1 further comprising a mode selector, wherein said microprocessor is responsive to said mode selector to operate in a first mode wherein said microprocessor maintains said selected rate and in a second mode, wherein said microprocessor operates said delivery member to set said rate in accordance with the position of said controller.

5. An injection device adapted to inject a therapeutic liquid into a patient under the control of a clinician, said device comprising:
   a handle adapted to be held by a clinician for administering the liquid;
   a pump adapted to selectively deliver the liquid to said handle;
   a motor adapted to operate said pump at a selected rate in accordance with a control signal;
   a control member operated by the clinician to select said rate, said control member having a first position associated with the selected rate and a second position; and
   a microprocessor coupled to said control member and adapted to generate said control signal after said control member has been operated and released by the clinician to generate said control signal;
   wherein said microprocessor is adapted to operate in a manual mode wherein said microprocessor selects a different rate for said delivery member for each position of said control member and a cruise control mode in which said microprocessor maintains the rate previously selected when said control member is returned to a neutral position.

6. The device of claim 5 wherein said control member is biased toward said second position.

7. The device of claim 6 further comprising an override switch operated by the clinician, said microprocessor being coupled to said override switch to generate a new control signal for said delivery member when said override switch is activated.

8. The injection device of claim 1 wherein said control member is a foot pedal.

9. An injection device comprising:
   a delivery member adapted to deliver a therapeutic liquid at a preselected rate;

a microprocessor adapted to generate control signals to said delivery member; and a control member operable by an operator to control the delivery of said therapeutic liquid, said control member having an operating position and a neutral position and being biased so that when released by the operator said control member returns to said neutral position, wherein said microprocessor cooperates with said control member to maintain the delivery of said therapeutic liquid at the preselected rate after said control member is released by the operator.

10. The injection device of claim 9 further comprising an override device adapted to generate an override signal, wherein said microprocessor is responsive to said override signal to stop the delivery of said therapeutic liquid.

11. The injection device of claim 9 wherein said microprocessor is adapted to monitor the position of said control member and to stop the delivery of the therapeutic liquid when the operator moves said control member from said neutral position during the delivery of the therapeutic liquid.

12. The injection device of claim 9 wherein said microprocessor is adapted to monitor said control member during a window starting when said control member is moved from said neutral position to said neutral position and to continue the delivery of the therapeutic agent if said control member is released within said window.

13. An injection device adapted to inject a therapeutic liquid into a patient under the control of a clinician, said device comprising:

a handle adapted to be held by a clinician for administering the liquid;

a pump adapted to selectively deliver the liquid to said handle;

a motor adapted to operate said pump in response to a control signal;

a control member operated by the clinician and having a first position and a second position, said control member being adapted to return automatically to said first position after said control member has been moved into said second position by the clinician to start the administration of said liquid and then has released said control member; and a microprocessor coupled to said control member and adapted to generate said control signal when said control member is moved from said first to said second position by the clinician, said microprocessor being adapted to maintain said control signal to keep said motor operating after said control member is released by the clinician.

14. The injection device of claim 13 further comprising an override device adapted to generate an override signal, wherein said microprocessor is responsive to said override signal to stop the delivery of said therapeutic liquid.

15. The injection device of claim 13 wherein said microprocessor is adapted to monitor the position of said control member and to stop the delivery of the therapeutic liquid when the operator moves said control member from said neutral position during the delivery of the therapeutic liquid.

* * * * *